United States Patent [19]

Martin et al.

[11] Patent Number: 4,933,493

[45] Date of Patent: Jun. 12, 1990

[54] INTERMEDIATES FOR THE PREPARATION OF 4-PHENYL-1,3-BENZODIAZEPINES

[75] Inventors: Lawrence L. Martin, Lebanon, N.J.; Manfred Worm, Wiesbaden-Naurod, Fed. Rep. of Germany; Charles A. Crichlow, Piscataway, N.J.

[73] Assignee: Hoechst-Roussel Pharmaceuticals Inc., Somerville, N.J.

[21] Appl. No.: 406,947

[22] Filed: Apr. 6, 1989

Related U.S. Application Data

[60] Division of Ser. No. 412,213, Aug. 27, 1983, Pat. No. 4,855,502, which is a continuation of Ser. No. 300,014, Sep. 8, 1981, abandoned, which is a continuation-in-part of Ser. No. 91,062, Nov. 5, 1979, Pat. No. 4,309,424, which is a continuation-in-part of Ser. No. 948,896, Oct. 5, 1978, abandoned.

[51] Int. Cl.$^5$ .......................... C07C 103/22
[52] U.S. Cl. .................. 564/185; 564/123; 564/219; 564/221
[58] Field of Search ............ 564/219, 221, 123, 185; 514/613, 617, 630

[56] References Cited

U.S. PATENT DOCUMENTS

| | | | |
|---|---|---|---|
| 3,138,639 | 6/1964 | Brossi et al. | 564/373 |
| 3,471,612 | 10/1969 | Goonewardene | 564/373 X |
| 3,510,560 | 5/1970 | Saunders | 564/373 X |
| 3,545,456 | 12/1970 | Goonewardene | 71/121 |
| 3,681,340 | 8/1972 | Rodriguez et al. | 540/567 |

FOREIGN PATENT DOCUMENTS

| | | |
|---|---|---|
| 790823 | 6/1962 | France . |
| 969977 | 9/1964 | United Kingdom ............... 564/373 |
| 1218135 | 1/1971 | United Kingdom . |

OTHER PUBLICATIONS

H. R. Rodriguez et al., J. Org. Chem., 33, 670 (1968).
K. Ogiu et al., Chem. Abs., 54, 18426 (e–i) (1960).
D. Buza et al., Chem Abs., 63, 16237 (1965).
G. A. Archer and L. H. Sternbach, Chem. Rev., 68, pp. 747–750 (1968).
Topics in Heterocyclic Chemistry, R. W. Castle, Ed., Wiley-Interscience, N.Y., N.Y., pp. 162–167 (1969).

*Primary Examiner*—Glennon H. Hollrah
*Assistant Examiner*—Scott C. Rand

[57] ABSTRACT

Novel 4-phenyl-1,3-benzodiazepines, novel intermediates thereof, and methods of preparing same are described. These benzodiazepines are useful as antidepressants, analgetics and anticonvulsants.

13 Claims, No Drawings

INTERMEDIATES FOR THE PREPARATION OF 4-PHENYL-1,3-BENZODIAZEPINES

This a division of application Ser. No. 412,213 filed Aug. 27, 1983, now U.S. Pat. No. 4,855,502 which is a continuation of application Ser. No. 300,014 filed Sept. 8, 1981 now abandoned, which is a continuation-in-part of application Ser. No. 091,062 filed Nov. 5, 1979 now U.S. Pat. No. 4,309,424 which is a continuation-in-part application of pending U.S. patent application Ser. No. 948,896, filed Oct. 5, 1978 now abandoned.

This invention relates to novel 4-phenyl-1,3-benzodiazepines, which are useful as antidepressants, analgetics, anticonvulsants, to methods of their preparation, to methods of treatment with pharmaceutically effective amounts thereof and to pharmaceutical compositions containing such a compound as an active ingredient. This invention also relates to novel compounds which are intermediates in the preparation of said 4-phenyl-1,3-benzodiazepines.

To the best of our knowledge the compounds of the present invention have not been heretofore made, described or suggested. Rodriguez et al., in U.S. Pat. No. 3,681,340 granted on Aug. 1, 1972 and entitled "1,3-Benzodiazepines," teaches that compounds of the formula

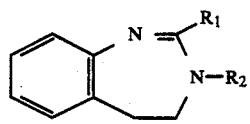

in which $R_1$ is hydrogen, free or etherified OH or SH, amino or an aliphatic, araliphatic or aromatic radical; $R_2$ is hydrogen or an acyl, aliphatic, araliphatic or aromatic radical; N-oxides and quaternaries and salts thereof, exhibit central nervous system depressing and coronary dilating effects.

The compounds of this invention have the formula

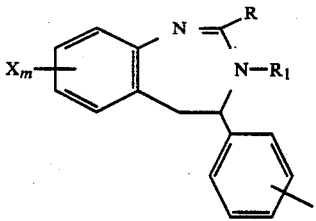

in which R is hydrogen or alkyl of from 1 to 5 carbon atoms; $R_1$ is hydrogen, alkyl of from 1 to 5 carbon atoms, cycloalkylalkyl of from 4 to 8 carbon atoms or aralkyl having from 1 to 5 carbon atoms in the alkyl moiety; X and Y are the same or different and each can be hydrogen, chlorine, bromine, fluorine, methoxy, alkyl of from 1 to 3 carbon atoms, hydroxy or trifluoromethyl; m is the integer 1 or 2; and n is the integer 1, 2 or 3. Also included within the scope of the present invention are the optical antipodes and the physioloigically acceptable salts of the above-depicted compounds.

Preferred compounds of the present invention are those in which R and $R_1$ are alkyl of from 1 to 5 carbon atoms. Particularly preferred compounds are those wherein R is methyl or ethyl and $R_1$ is methyl.

Novel intermediate compounds, which are also the subject of this invention, utilized in the preparation of the benzodiazepines of this invention, have the formula

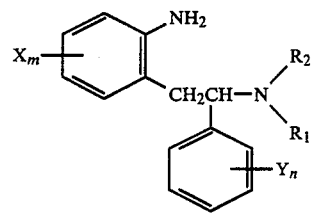

in which $R_1$ is hydrogen, alkyl of from 1 to 5 carbon atoms, cycloalkylalkyl of from 4 to 8 carbon atoms or aralkyl having 1 to 5 carbon atoms in the alkyl moiety; $R_2$ is hydrogen or alkyl of from 1 to 5 carbon atoms with the proviso that $R_2$ is hydrogen when $R_1$ is alkyl; or a group of the formula

wherein $R_3$ is hydrogen, alkyl of from 1 to 4 carbon atoms, cycloalkyl of from 3 to 7 carbon atoms or aryl; and X, Y, m and n are as previously defined.

Additional novel intermediates of the present invention include compounds of the formula

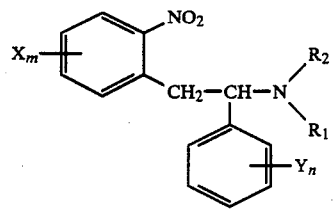

in which $R_1$ is hydrogen, alkyl of from 1 to 5 carbon atoms, cycloalkylalkyl of from 4 to 8 carbon atoms or aralkyl having 1 to 5 carbon atoms in the alkyl moiety; $R_2$ is hydrogen or alkyl of from 1 to 5 carbon atoms with the proviso that $R_2$ is hydrogen when $R_1$ is alkyl of from 1 to 5 carbon atoms; or a group of the formula

wherein $R_3$ is hydrogen, alkyl of from 1 to 4 carbon atoms, cycloalkyl of from 3 to 7 carbon atoms or aryl; X and Y are the same or different and each can be hydrogen, chlorine, bromine, fluorine, methoxy, alkyl of from 1 to 3 carbon atoms, hydroxy or trifluoromethyl; m is the integer 1 to 2 and n is the integer, 1, 2 or 3; and

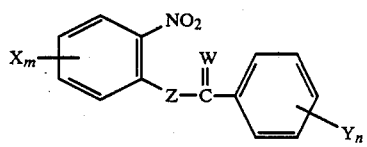

in which Z is methylene or a group of the formula

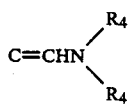

wherein R₄ is alkyl of from 1 to 5 carbon atoms; W is oxo or a group of the formula N—OR₅ wherein R₅ is hydrogen or alkanoyl of from 1 to 5 carbon atoms; X and Y are the same or different and each can be hydrogen, chlorine, bromine, fluorine, methoxy, alkyl of from 1 to 3 carbon atoms, hydroxy or trifluoromethyl; and m is the integer 1 or 2; n is the integer 1, 2 or 3.

In the above intermediates, i.e., the phenethylamines and the corresponding acyl derivatives thereof, preferred compounds are those in which $R_1$ is alkyl of from 1 to 5 carbon atoms. Particularly preferred compounds are those in which $R_1$ is methyl.

The physiologically acceptable salts of the present invention are acid addition salts which may be prepared from inorganic acids such as hydrochloric, hydrobromic, sulfuric, nitric, phosphoric and perchloric acids, as well as from organic acids such as tartaric, citric, acetic, succinic, maleic, fumaric and oxalic.

As used throughout the specification and appeneded claims, the term "alkyl" shall mean a straight or branched chain hydrocarbon group containing no unsaturation and having from 1 to 5 carbon atoms. Examples of alkyl groups are methyl, ethyl, propyl, isopropyl, butyl, isobutyl, sec-butyl, tert-butyl, pentyl, isopentyl, neopentyl, tert-pentyl and the like. The term "cycloalkyl" shall mean a saturated hydrocarbon group possessing at least one carbocyclic ring and having from 3 to 7 carbon atoms. Examples of cycloalkyl groups are cyclopropyl, cyclobutyl, cyclopentyl, cyclohexyl, cycloheptyl and the like. The term "cycloalkylalkyl" refers to a radical formed by attachment of an alkyl function to a cycloalkyl group. Examples of cycloalkylalkyl radicals include cyclopropylethyl, cyclopropylpropyl, cyclopropylbutyl, cyclopropylpentyl, cyclobutylmethyl, cyclobutylpropyl, cyclobutylbutyl, cyclopentylmethyl, cyclopentylethyl, cyclopentylpropyl, cyclohexylethyl, cycloheptylmethyl and the like. The term "aryl" shall mean phenyl or phenyl substituted with one or more chloro, bromo, fluoro, methoxy, alkyl of from 1 to 5 carbon atoms, hydroxy or trifluoromethyl groups. The term "aralkyl" refers to a radical formed by attachment of an alkyl function to an aryl moiety. The term "alkanoyl" shall mean the residue of an alkylcarboxylic acid (alkanoic acid) having from 1 to 5 carbon atoms formed by removal of the hydroxy group of the carboxylic acid moiety. Examples of alkanoyl groups include formyl, acetyl, propionyl, butyryl and the like.

The compounds of the present invention can be prepared according to the following sequence of reactions in which R, $R_1$, $R_2$, $R_3$, $R_4$, $R_5$, W, X, Y, Z, m and n are as previously defined, unless other wise indicated.

1. A 2-(2-nitrophenyl)acetophenone of the formula

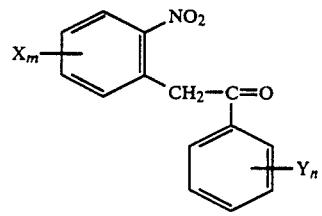

is converted to an oxime of the formula

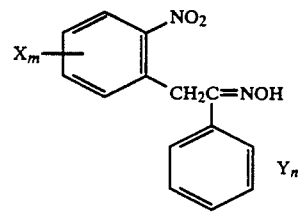

by any convenient method known to the art. A preferred method involves refluxing the acetophenone in a mixute of ethyl alcohol, aqueous sodium acetate and hydroxylamine.

2. A compound of formula II is acylated with an alkanoic acid anhydride to provide the corresponding oxime alkanoate of the formula

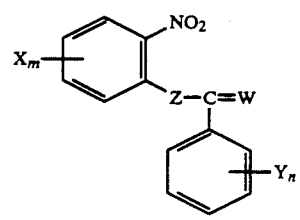

in which Z is methylene and W is NOR₅ wherein R₅ is alkanoyl of from 1 to 5 carbon atoms. Suitable alkanoic acid anhydrides include mixed formic acidacetic acid anhydride, butyric acid anhydride, pentanoic acid anhydride, hexanoic acid anhydride and the like. Acetic acid anhydride is preferred.

3. A compound of formula III is carefully reduced to provide the corresponding 2-nitro-α-phenylphenethylamine of the formula

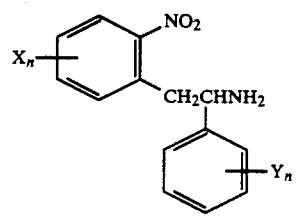

The reducing agent used in this step must be compatible with the phenyl nitro group. Diborane is preferred. Additionally, this reduction is carried out in the presence of a solvent such as tetrahydrofuran and at a low temperature of from about 0° C. to about 30° C. or at ambient temperature.

4. A compound of formula IV is further reduced to provide the corresponding 2-amino-α-phenylphenethylamine, a novel intermediate compound of the present invention, of the formula

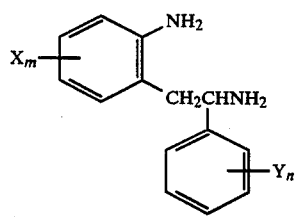 V

A preferred reducing method involves hydrogenation with a palladium on carbon catalyst or Adam's catalyst. Also, other chemical reducing methods are suitable such as the use of tin and hydrochloric acid.

5. A compound of formula IV is converted by any method known to the art, to the corresponding amide of the formula

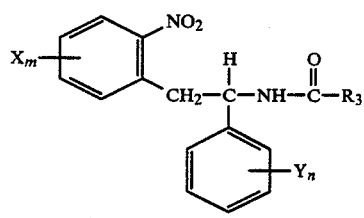 VI

This conversion is carried out with an appropriate carboxylic acid anhydride or halide in the presence of a suitable solvent. Appropriate carboxylic acid anhydrides include acetic anhydride, propionic anhydride, butyric anhydride and the like. Appropriate carboxylic acid halides include cyclohexanecarbonyl chloride, cyclopopanecarbonyl chloride, cyclobutanecarbonyl chloride, cyclopentanecarbonyl chloride, cycloheptanecarbonyl chloride and the like. Carboxylic acid anhydrides are preferred. Acetic anhydride is most preferred. Additionally, when $R_3$ is hydrogen, a preferred method is the mixed anhydride procedure utilizing a mixture of acetic anhydride and formic acid at a temperature of from about 0° C. to 100° C. with a suitable solvent such as benzene. Alkylformates may also be utilized to prepare the formamides of formula VI, i.e., the compounds of formula VI wherein $R_3$ is hydrogen. Suitable alkylformates include methyl formate, ethyl formate, propyl formate, butyl formate and the like. When methyl formate is employed, it is desirable to carry out the reaction at an elevated temperature of from about 60°–100° C. in a pressure vessel such as a Paar bomb. A reaction temperature of about 80° C. is preferred.

6. A compound of formula VI is reduced in a manner consistent with the procedure of step 3, above, to provide the corresponding N-alkyl-α-phenyl-2-nitrophenylethylamine of the formula

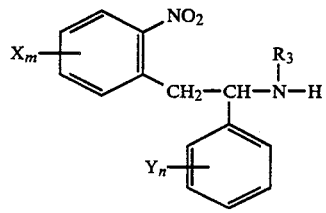 VII in which $R_1$ is alkyl of from 1 to 5 carbon atoms, cycloalkylalkyl of from 4 to 8 carbon atoms or aralkyl.

7. A compound of formula VII is reduced in a manner consistent with the procedure of step 4, above, to provide the corresponding N-alkyl-2-amino-α-phenylphenethylamine, a novel intermediate of the present invention, of the formula

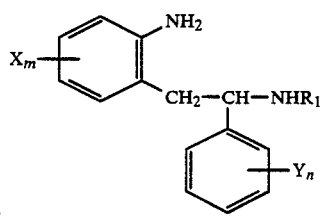 VIII

8. A compound of formula V or VIII is cyclized with a compound of the formula

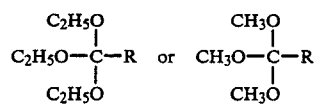

to provide the corresponding 1,3-benzodiazepine, a compound of the present invention, of the formula

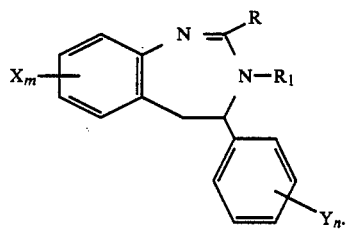 IX

This cyclization is carried out in the presence of an acid catalyst such as ethanolic hydrochloric acid at a temperature of from 25° C. to reflux of the reaction mixture.

In an alternative process, the compounds of the present invention are prepared according to the following reaction sequence in which R, $R_1$, $R_2$, $R_3$, X, Y, m and n are as previously defined, unless otherwise indicated.

1'. A compound of formula VII is acylated in a manner consistent with the procedure of step 5, supra, to provide the corresponding N-alkyl-N-alkanoyl-α-phenyl-2-nitrophenethylamine of the formula

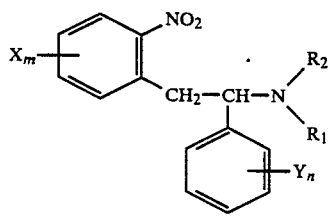

in which $R_1$ is alkyl of from 1 to 5 carbon atoms, cycloalkylalkyl of from 4 to 8 carbon atoms or aralkyl and $R_2$ is a group of the formula

wherein $R_3$ is hydrogen or alkyl of from 1 to 4 carbon atoms.

2'. A compound of formula X is reduced in a manner consistent with the procedure of step 6, supra, to provide the corresponding N-alkyl-N-alkanoyl-2-amino-α-phenylphenethylamine of the formula

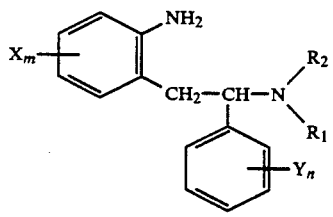

in which $R_1$, $R_2$ and $R_3$ are as described in Step 1'.

3'. A compound of formula XI is converted to the 1,3-benzodiazepine of formula IX wherein R and $R_3$ are the same. The conversion is conveniently performed by treating XI with a cyclodehydrating agent, neat or in the presence of a suitable solvent. Among cyclodehydrating agents there may be mentioned phosphorous pentoxide, phsophorous pentachloride, phosphorous trichloride, phosphorous oxychloride, boron trifluoride, boron trichloride and the like. Among suitable solvents there may be mentioned halocarbons such as, for example, dichloromethane, chloroform, 1,2-dichloroethane and the like, and aromatic hydrocarbons such as benzene, toluene, oxylene and the like. Phosphorous oxychloride is the preferred cyclodehydrating agent and dichloromethane is the preferred solvent. The reaction temperature is not narrowly critical. Generally, the reaction mixture is heated at the reflux temperature of the solvent to promote a reasonable rate of reaction. When phosphorous oxychloride and dichloromethane are employed, the cyclodehydration proceeds satisfactorily at the reflux temperature of the solvent.

In each of the above reaction steps, optimum conditions depend upon starting materials, solvents, catalysts and other reaction components, as will become more apparent in the examples given below.

Optical antipodes can be prepared by resolution with common resolving agents such as optically pure tartaric and camphor sulfonic acids or synthesized from optically pure precursors.

Compounds depicted in formula I are either generally available or prepared as described below. O. Hromatka et al., Montsh, 100, 469 (1969) describe the following synthesis in which X is chlorine or bromine:

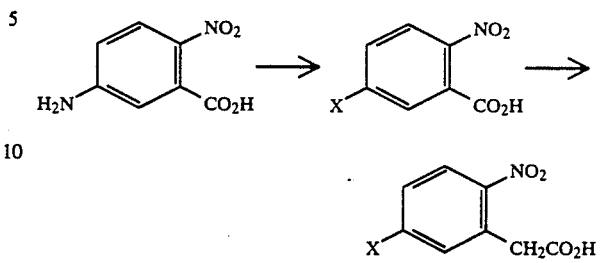

Routine manipulation of this synthesis would provide corresponding compounds in which X is fluorine, hydroxy, methoxy or cyano.

Additionally, 2,4-dinitroaniline can be treated by routine methods to ultimately provide a compound of the formula

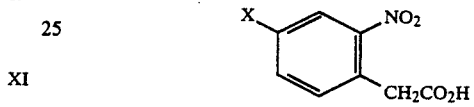

through the following precursors:

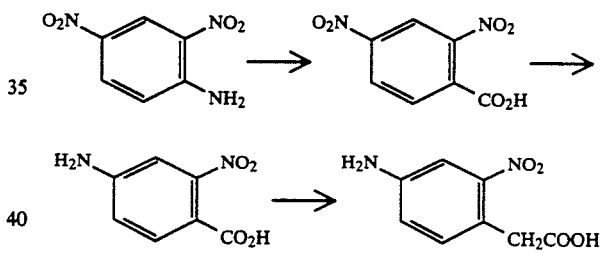

Thereafter, compounds of formula I can be prepared by Friedel Crafts acylation as follows:

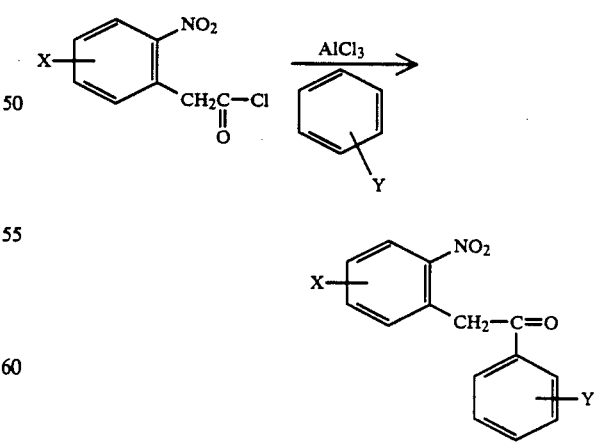

Compounds of formula I are also prepared by the process described by E. E. Garcia and R. I. Fryer in J. Heterocyclic Chemistry, 11, 219 (1974). In this process, an enamine of the formula

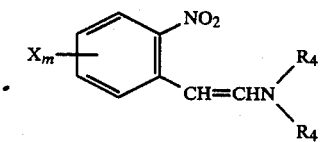

in which R₄, X and m are as described herein, is condensed with a benzoyl halide, e.g., a benzoyl chloride of the formula

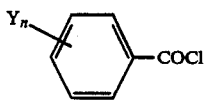

in which Y and n are as hereinbeforedescribed to afford an enaminoketone of the formula

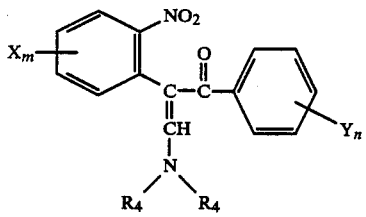

in which R₄, X, Y, m and n are as above, i.e., a compound of the formula

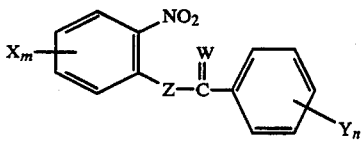

in which Z is

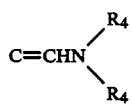

wherein R₄ is alkyl of from 1 to 5 carbon atoms, W is oxo and X, Y, m and n are as described above. The enaminoketone is then hydrolyzed and deformlayed to I.

The utility of the compounds of the present invention in the treatment of depression in mammals is demonstrated by their ability to inhibit tetrabenazine induced depression in mice [International Journal of Neuropharmacology, 8, 73 (1969)], a standard assay for useful antidepressant properties. Thus, for instance, an intraperitoneal dose of 1.5 mg/kg of body weight and an oral dose of 2.1 mg/kg of body weight of 4,5-dihydro-2,3-dimethyl-4-phenyl-3H-1,3-benzodiazepine hydrochloride each demonstrate a 50% inhibition of ptosis of tetrabenazine-induced depression in mice. Also, an intraperitoneal dose of 9.7 mg/kg of body weight of 4,5-dihydro-3-methyl-4-phenyl-3H-1,3-benzodiazepine hydrochloride and an intraperitoneal dose of 20 mg/kg of body weight of 4,5-dihydro-4-phenyl-3H-1,3-benzodiazepine hydrochloride demonstrate a similar inhibition in this assay. Finally, an intraperitoneal dose of 20 mg/kg body weight of 4,5-dihydro-2-methyl-4-phenyl-3H,1,3-benzodiazepine hydrochloride demonstrates a 30% inhibition in this assay. These data indicate that the compounds of the present invention would be useful as anti-depressants in mammals when administered in amounts ranging from 0.01 to 100 mg/kg of body weight per day.

Compounds of the present invention are useful as analgetics due to their ability to alleviate pain in mammals, as demonstrated in the phenyl-2-quinone writhing assay in mice, a standard assay for analgesia [Proc. Soc. Exptl. Biol. Med., 95, 729 (1957)]. Thus, for example, a subcutaneous dose of 21.3 mg/kg of body weight of 4,5-dihydro-4-phenyl-3H-1,3-benzodiazepine hydrochloride demonstrates a 50% inhibition of writhing produced in this assay. This datum illustrates that compounds of this invention are useful for alleviating pain in mammals when administered in amounts ranging from about 0.01 to about 100 mg/kg of body weight per day.

Compounds of the present invention are further useful as anticonvulsant agents for mammals, as determined by Woodbury, L. A. and Davenport, V. D. [Arch. Int. Pharmacodynam, 92, pp 97–107 (1952)]. For example, 4,5-dihydro-3-methyl-4-phenyl-3H-1,3-benzodiazepine hydrochloride and 4,5-dihydro-4-phenyl-3H-1,3-benzodiazepine hydrochloride at an intraperitoneal dose of 13.4 and 19.4 mg/kg of body weight, respectively, each produce a 50% protection from the effect of supramaximal electroshock. These data illustrate that compounds of the present invention are useful in treating convulsions in mammals when administered in amounts ranging from about 0.01 to about 100 mg/kg of body weight per day.

Compounds of this invention include:
7-chloro-4,5-dihydro-2,3-dimethyl-4-phenyl-3H,1,3-benzodiazepine;
2,3-diethyl-7,8-difluoro-4,5-dihydro-4-phenyl-3H-1,3-benzodiazepine;
4,5-dihydro-2,3-dimethyl-4-(3-trifluoromethylphenyl)-3H-1,3-benzodiazepine;
4,5-dihydro-2-ethyl-4-phenyl-3H-1,3-benzodiazepine;
4,5-dihydro-4-phenyl-7-trifluoromethyl-3H-1,3-benzodiazepine;
4,5-dihydro-2,3-dimethyl-6-methoxy-4-(2-methoxyphenyl)-3H-1,3-benzodiazepine;
4,5-dihydro-2-isopropyl-4-phenyl-3-n-propyl-3H-1,3-benzodiazepine;
7,8-dibromo-4,5-dihydro-2,3-dimethyl-4-(2-methylphenyl)-3H-1,3-benzodiazepine;
4,5-dihydro-9-hydroxy-4-(3-n-propylphenyl)-3H-1,3-benzodiazepine;
7,8-dibromo-4-(2,3-difluorophenyl)-4,5-dihydro-2,3-dimethyl-3H-1,3-benzodiazepine;
4-(4-chlorophenyl)-4,5-dihydro-2,3-dimethyl-3H-1,3-benzodiazepine;
4-(4-chlorophenyl)-4,5-dihydro-2-ethyl-3-methyl-3H-1,3-benzodiazepine;
4,5-dihydro-2,3-dimethyl-4-(2-fluorophenyl)-3H-1,3-benzodiazepine;
4,5-dihydro-2-ethyl-4-(2-fluorophenyl)-3-methyl-3H-1,3-benzodiazepine;
4-(4-bromophenyl)-4,5-dihydro-2,3-dimethyl-3H-1,3-benzodiazepine;
4-(4-bromophenyl)-4,5-dihydro-2-ethyl-3-methyl-3H-1,3-benzodiazepine;
4,5-dihydro-2,3-dimethyl-4-(4-trifluoromethylphenyl)-3H-1,3-benzodiazepine;

4,5-dihydro-2-ethyl-3-methyl-4-(4-trifluoromethylphenyl)-3H-1,3-benzodiazepine;
4-(3,4-dichlorophenyl)-4,5-dihydro-2,3-dimethyl-3H-1,3-benzodiazepine;
4-(3,4-dichlorophenyl)-4,5-dihydro-2-ethyl-3-methyl-3H-1,3-benzodiazepine;
7-chloro-4,5-dihydro-2,3-dimethyl-4-phenyl-3H-1,3-benzodizepine;
7-chloro-4,5-dihydro-2-ethyl-3-methyl-4-phenyl-3H-1,3-benzodiazepine;
8-chloro-4,5-dihydro-2,3-dimethyl-4-phenyl-3H-1,3-benzodiazepine;
8-chloro-4,5-dihydro-2-ethyl-3-methyl-4-phenyl-3H-1,3-benzodiazepine;
4,5-dihydro-2,3-dimethyl-7-methoxy-4-phenyl-3H-1,3-benzodiazepine;
4,5-dihydro-2-ethyl-7-methoxy-3-methyl-4-phenyl-3H-1,3-benzodiazepine;
4,5-dihydro-2,3-dimethyl-8-methoxy-4-phenyl-3H-1,3-benzodiazepine;
4,5-dihydro-2-ethyl-8-methoxy-3-methyl-4-phenyl-3H-1,3-benzodiazepine;
4,5-dihydro-7,8-dimethoxy-2,3-dimethyl-4-phenyl-3H-1,3-benzodiazepine;
4,5-dihydro-7,8-dimethoxy-2-ethyl-3-methyl-4-phenyl-3H-1,3-benzodiazepine;
6-chloro-4,5-dihydro-2,3-dimethyl-4-phenyl-3H-1,3-benzodizepine;
6-chloro-4,5-dihydro-2-ethyl-3-methyl-4-phenyl-3H-1,3-benzodiazepine;
7-chloro-4,5-dihydro-2,3-dimethyl-4-(2-fluorophenyl)-3H-1,3-benzodiazepine;
7-chloro-4,5-dihydro-2-ethyl-4-(2-fluorophenyl)-3-methyl-3H-1,3-benzodiazepine;
4,5-dihydro-2-ethyl-4-(4-fluorophenyl)-3-methyl-3H-1,3-benzodiazepine;
4,5-dihydro-2-ethyl-4-(4-methylphenyl)-3-methyl-3H-1,3-benzodiazepine;
4,5-dihydro-2,3-dimethyl-4-(4-fluoro-2-methylphenyl)-3H-1,3-benzodiazepine;
4,5-dihydro-2-ethyl-4-(4-fluoro-2-methylphenyl)-3-methyl-3H-1,3-benzodiazepine;
4,5-dihydro-2,3-dimethyl-4-(2-fluoro-4-methylphenyl)-3H-1,3-benzodiazepines;
4,5-dihydro-2-ethyl-4-(2-fluoro-4-methylphenyl)-3-methyl-3H-1,3-benzodiazepine;
3-butyl-2-sec-butyl-4,5-dihydro-4-phenyl-3H-1,3-benzodiazepine;
4,5-dihydro-2,3-diisobutyl-4-phenyl-3H-1,3-benzodiazepine;
2-tert-butyl-4,5-dihydro-4-phenyl-3H-1,3-benzodiazepine;
4,5-dihydro-2,3-diisopentyl-4-phenyl-3H-1,3-benzodiazepine;
4,5-dihydro-3-pentyl-2-tert-pentyl-4-phenyl-3H-1,3-benzodiazepine;
4,5-dihydro-3-neopentyl-4-phenyl-3H-1,3-benzodiazepine;
7-chloro-4-(2-chlorophenyl)-4,5-dihydro-2,3-dimethyl-3H-1,3-benzodiazepine;
7-chloro-4-(2-chlorophenyl)-4,5-dihydro-2-ethyl-3-methyl-3H-1,3-benzodiazepine;
4,5-dihydro-2-tert-pentyl-4-phenyl-3H-1,3-benzodiazepine;
3-cyclopropylmethyl-4,5-dihydro-2-methyl-4-phenyl-3H-1,3-benzodiazepine;
3-cyclopentylmethyl-4,5-dihydro-2-methyl-4-phenyl-3H-1,3-benzodiazepine; and
3-cyclobutylethyl-4,5-dihydro-2-ethyl-4-phenyl-3H-1,3-benzodiazepine.

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent, and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied to be between 0.5 and about 5% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

EXAMPLE 1 a. A stirring mixture of 43.0 g of 2-(2-nitrophenyl)-acetophenone, 200 ml of 95% ethyl alcohol, 31.2 g of sodium acetate and 24.3 g of hydroxylamine hydrochloride in 100 ml of water is refluxed for 1 hour and then permitted to stand for 16 hours. Thereafter, the precipitate is collected by suction filtration and the filter cake is sequentially washed with 100 ml of 60% aqueous ethyl alcohol, two 100 ml portions of water, dried and recrystallized from 95% ethyl alcohol to provide nearly colorless crystals, mp 119°–121° C., of 2-(2-nitrophenyl)-acetophenone oxime. [The 2-(2-nitrophenyl)acetophenone starting material is reported in Chem., Absts., 63, 16237 g (1965)].

b. A stirring solution of 5.0 g of 2-(2-nitrophenyl)-acetophenone oxime in 10 ml of potassium hydroxide dried pyridene is treated with 5 ml of acetic anhydride in three equal portions. After total addition, the solution is heated on a steam bath for 45 minutes with the exclusion of moisture and then decanted into 50 ml of ice water. An oil separates which solidifies with continued stirring. The solid is successively collected by vacuum filtration, washed with water, dried under vacuum over potassium hydroxide pellets and recrystallized from 95% ethyl alcohol to provide nearly colorless crystals, mp 63°–66° C., of 2-(2-nitrophenyl)acetophenone oxime acetate.

c. 150 ml of a 1M solution of diborane in tetrahydrofuran are added to a stirring mixture of 9.0 g of 2-(2-nitrophenyl)-acetophenone oxime acetate and 150 ml of tetrahydrofuran over a 20 minute span with ice-water bath cooling. After total addition, the reaction mixture is stirred for 48 hours at ambient temperature before carefully adding, with stirring, 150 ml of a 5% hydrochloric acid solution. After this total addition the tetrahydrofuran is distilled under reduced pressure and the residue is extracted thrice with 200 ml portions of ether. The aqueous phase is basified with 50% sodium hydroxide and the alkaline phase is extracted thrice with 300 ml portions of ether. The combined ether extracts are dried and then concentrated, leaving an oil which, in ether, is converted to its hydrochloric acid salt. The salt is collected by vacuum filtration and then washed thoroughly with ether. The dried salt is recrystallized from methyl alcohol to provide colorless crystals, mp 261°–263° C., dec., of 2-nitro-α-phenylphenethylamine hydrochloride.

d. 19.4 g of 25% (W/W) a sodium methoxide in methyl alcohol solution are added to a suspension of 19.6 g of 2-nitro-α-phenylphenethylamine hydrochloride in 100 ml of ethyl alcohol. After the addition, the mixture is stirred with steam bath warming before being filtered. The filter cake is washed with 70 ml of 95% ethyl alcohol and the filtrates are combined and then transferred into a 500 ml Parr hydrogenation bottle which had been charged with 2.0 g of a 10% palladium/carbon catalyst and 20 ml of 95% ethyl alcohol. The mixture is hydrogenated for 3 hours at 50 psig at ambient temperature. Thereafter, the mixture is suction filtered and the filtrate is evaporated, leaving an orange oil which is dissolved in 100 ml of chloroform. The chloroform solution is washed twice with 100 ml portions of 5% sodium hydroxide solution. All the chloroform solutions are combined and then sequentially dried, filtered and the filtrate is evaporated, leaving an orange oil which is diluted with 12 ml of cyclohexane. This solution is seeded with a crystalline product obtained from the previously obtained crude oil by crystallization of a sample from a small amount of cyclohexane, stirred vigorously and permitted to stand at 5° C. for 48 hours. Thereafter, the mother liquid is decanted and the crystalline precipitate is pulverized and collected in a Buchner funnel. The filter cake is washed with cyclohexane, dried and recrystallized from cyclohexane to provide colorless crystals, mp 43°–44° C., of 2-amino-α-phenylphenethylamine.

e. 70 ml of hydrochloric acid saturated absolute ethyl alcohol are added dropwise to a stirred mixture of 7.0 g of 2-amino-α-phenylphenethylamine hydrochloride, salt of step d, and 70 ml of triethylorthoformate. After total addition, the reaction mixture is refluxed, in the absence of moisture, for 16 hours and then successively cooled, diluted with ether and suction filtered to provide a crystalline material which is dried under vacuum for 5 hours. The product is recrystallized from a methyl alcohol-ether mixture and the resulting crystals are washed with ether and then dried, providing colorless crystals, mp 185°–187° C., of 4,5-dihydro-4-phenyl-3H-1,3-benzodiazepine hydrochloride.

Analysis: Calculated for $C_{15}H_{14}N_2 \cdot HCl$: 69.62%C; 5.84%H; 10.82%N. Found: 69.71%C; 5.84%H; 10.83%N.

EXAMPLE 2

76.6 of triethylorthoacetate are added to a refluxing solution of 7.1 g of 2-amino-α-phenylphenethylamine (Example 1d) and 91 ml of hydrochloric acid saturated absolute ethyl alcohol. After this addition, refluxing is continued for 16 hours before the mixture is permitted to cool. The cooled mixture is diluted with 1.5 liter of ether and then refrigerated in the absence of moisture for 72 hours. Thereafter, the solvent is decanted and the precipitate is covered with ether. The precipitate is collected by suction filtration and then dried. The dried product is recrystallized from an ethyl alcohol-ether mixture to provide, after drying under vacuum at 40° C., colorless crystals mp 194°–197° C., of 4,5-dihydro-2-methyl-4-phenyl-3H-1,3-benzodiazepine hydrochloride.

Analysis: Calculated for $C_{16}H_{16}N_2 \cdot HCl$: 70.40%C, 6.28%H; 10.26%N. Found: 70.42%C; 6.29%H; 10.22%N.

EXAMPLE 3 a. A mixture of 27.6 g of acetic anhydride and 16.7 ml of formic acid is heated at 50°–67° C. for 15 minutes and then cooled to 10°–15° C. A solution of 31.8 g of 2-nitro-α-phenylphenethylamine, free base of Example 1c, in benzene is added at such a rate as to maintain the reactions mixture's temperature at 10°–15° C. After total addition, the suspension is stirred for 48 hours at 50° C. and then stirred for an additional 48 hours at ambient temperature. Thereafter, the material is collected by suction filtration and then rinsed well with ether. The filtrate is evaporated under reduced pressure and the resulting solid is combined with the filter cake. The combined solid is dried under vacuum at 40° C. for 2 hours and the dried material is dissolved in methylene chloride and this solution is successively washed with 5% hydrochloric acid solution, washed with water, dried, filtered and evaporated leaving a solid. The solid is recrystallized from ethyl alcohol to provide, after drying under vacuum at 90° C., light yellow crystals, mp 151°–153° C., of N-formyl-2-nitro-α-phenylphenethylamine.

b. A solution of 96 ml of 1M diborane in tetrahydrofuran and 50 ml of tetrahydrofuran is added dropwise to an ice cold suspension of 13 g of N-formyl-2-nitro-α-phenylphenethylamine in 150 of tetrahydrofuran. After the effervescence ceases, 28 ml of 5N hydrochloric acid are added dropwise.

Thereafter, the solvent is removed under reduced pressure and the resulting oily mixture is basified with a 50% sodium hydroxide aqueous solution. The basified mixture is extracted with several portions of ether and the combined ether extracts are successively dried, filtered and evaporated, providing an oil. The oil is dissolved in benzene and this solution is treated with ethereal hydrochloric acid. The solvent is removed and the resulting material is recrystallized from isopropyl alcohol to provide, after drying over xylene for 24 hours, light yellow crystals, mp 192°–196° C., of N-methyl-2-nitro-α-phenylphenethylamine hydrochloride.

c. A solution of 0.5 g of N-methyl-2-nitro-α-phenylphenethylamine hydrochloride in 20 ml of ethyl alcohol is added to a Parr hydrogenation bottle previously charged with 0.2 g of platinum dioxide, Adam's catalyst, and 5 ml of ethyl alcohol. This is pressurized to 50 psi with hydrogen for 5 minutes, then to 15 psi and placed on a Parr shaker for 30 minutes. The mixture is filtered through a fine sintered glass funnel and the filtrate is evaporated. The resulting material is recrystallized from isopropyl alcohol to provide, after drying, colorless crystals, mp 190°–191° C., of 2-amino-N-methyl-α-phenylphenethylamine hydrochloride.

d. 40 ml of hydrochloride acid saturated absolute ethyl alcohol are added dropwise to a stirred mixture of 4.0 g of 2-amino-N-methyl-α-phenylphenethylamine hydrochloride and 40 ml of triethyl orthoformate. After this addition, the resulting solution is successively refluxed for 16 hours, cooled, diluted with ether and suction filtered, providing a crystalline material. The material is recrystallized by dissolving in methyl alcohol, filtering and diluting with ether to provide, after drying, colorless crystals, mp 251°–254° C., of 4,5-dihydro-3-methyl-4-phenyl-3H-1,3-benzodiazepine hydrochloride.

Analysis: Calculated for $C_{16}H_{16}N_2 \cdot HCl$: 70.45%C; 6.28%H; 10.26%N. Found: 70.44%C; 6.19%H; 10.50%N.

EXAMPLE 4

40 ml of hydrochloric acid saturated absolute ethyl alcohol are added dropwise to a stirred mixture of 4.0 g of 2-amino-N-methyl-α-phenylphenethylamine hydrochloride (Example 3c) and 40 ml of triethyl orthoacetate. After total addition the reaction mixture is successively refluxed for 2 hours, cooled, diluted with ether and filtered to collect a solid material. The material is recrystallized from a methyl alcohol-ether mixture to provide a white, solid material which is dried to provide a crystalline product, mp 240°–243° C., of 4,5-dihydro-2,3-dimethyl-4-phenyl-3H-1,3-benzodiazepine hydrochloride.

Analysis: Calculated for $C_{17}H_{18}N_2 \cdot HCl$; 71.19%C; 6.68%H; 9.77%N. Found: 71.43%C; 6.59%H; 9.73%N.

EXAMPLE 5

90 ml of Ethanolic hydrogen chloride is added dropwise to a stirred suspension of 9.00 g of 2-amino-α-phenyl-N-propylphenethylamine in 90 ml of triethyl orthoacetate. After complete addition, the mixture is refluxed for 2 hours. The ethanol is slowly distilled from the mixture and additional ethanolic hydrogen chloride (50 ml) is added. The mixture is then distilled to a volume of 20–30 ml. 100 ml of ether is added causing precipitation of the hydrochloride salt. The salt is collected, washed with ether (100 ml) and dried to give white crystals, mp 272°–275° C. of 4,5-dihydro-2-methyl-4-phenyl-3-propyl-3H-1,3-benzodiazepine hydrochloride.

Analysis: Calculated for $C_{19}H_{22}N_2HCl$: 72.48%C; 7.36%H; 8.90%N. Found: 72.25%C; 7.34%H; 8.90%N.

EXAMPLE 6

250 g of 2-Amino-N-cyclohexylmethyl-α-phenylphenethylamine dihydrochloride is heated in 2.40 ml of refluxing triethyl orthoacetate and 0.75 ml of acetic acid for 1.5 hours, after which the volatile components are distilled from the reaction mixture. The residual solvents are removed in vacuo (aspirator). The resulting solid is dissolved in 25 ml of 5% hydrochloric acid and 10 ml of methylene chloride. The biphasic mixture is poured onto 100 ml of water and the resulting biphasic mixture is extracted with methylene chloride (2×100 ml). The combined methylene chloride extracts are dried over anhydrous magnesium sulfate and the methylene chloride evaporated affording a pale yellow oil. The oil is dissolved in 50 ml of ether. Etherial hydrogen chloride is added precipitating the salt as an oily solid. The ether is evaporated and the oily solid is dissolved in 10 ml of methanol. 50 ml of ethyl acetate is then added. The methanol is boiled from solution, followed by cooling. Hexane is slowly added until a slight cloudiness appears. Scratching produces white crystals, mp 256°–258° C., of 3-cyclohexylmethyl-2-methyl-4-phenyl-3H-1,3-benzodiazepine hydrochloride.

Analysis: Calculated for $C_{23}H_{28}N_2 \cdot HCl$: 74.88%C; 7.92%H; 7.59%N. Found: 74.71%C; 8.02%H; 7.55%N.

EXAMPLE 7

6.00 g of 2-Amino-N-methyl-α-phenylphenethylamine dihydrochloride is heated in 8.1 ml of refluxing triethyl orthopropionate and 2.4 ml of acetic acid for 2 hours, after which the volatile solvents are distilled from the reaction mixture. The less volatile solvents are then distilled in vacuo (aspirator) from the mixture. The resulting oil is dissolved in 20 ml of 5% hydrochloric acid and the acidic solution is poured onto 100 ml of water. The aqueous phase is washed with 100 ml of ether, basified with 50% sodium hydroxide and extracted with dichloromethane (2×200 ml). The combined dichloromethane extracts are dried over anhydrous magnesium sulfate and the dichloromethane evaporated affording a colorless oil. The oil is dissolved in 100 ml of ether. Ethereal hydrochloric acid is added precipitating the salt as an oily solid. The ether is evaporated from the mixture and the resulting oil is recrystallized from 20 ml of acetone providing crystals, mp 250°–255° C. dec, of 2-ethyl-3-methyl-4-phenyl-3H-1,3-benzodiazepine hydrochloride.

Analysis: Calculated for $C_{18}H_{20}N_2 \cdot HCl$: 71.87%C; 7.04%H; 9.31%N. Found: 71.69%C; 6.87%H; 9.29%N.

EXAMPLE 8

6.00 g of 2-Amino-N-benzyl-α-phenylphenethylamine dihydrochloride is heated in 17.64 ml of refluxing triethyl orthoacetate and 5.58 ml of acetic acid for 24 hours, after which the solvents are distilled from the reaction flask first at atmospheric pressure followed by distillation in vacuo (aspirator). The resulting oil is dissolved in 5% hydrochloric acid: methylene chloride (20 ml: 10 ml) and poured onto 100 ml of water containing 10 ml of 37% hydrochloric acid. The biphasis acidic mixture is washed with ether. (2×100 ml), basified with 10 ml of 50% sodium hydroxide and extracted with methylene chloride (2×200 ml). The combined methylene chloride extracts are dried over anhydrous magnesium sulfate and the methylene chloride evaporated. The resulting oil is dissolved in ether (100 ml). Ethereal hydrochloric acid (20 ml) is added precipitating the hdyrochloride salt. The precipitate is collected and washed with 60 ml of hot acetone affording white crystals, mp 245°–247° C., of 3-benzyl-4,5-dihydro-2-methyl-4-phenyl-3H-1,3-benzodiazepine hydrochloride.

Analysis: Calculated for $C_{23}H_{22}N_2 \cdot HCl$: 76.03%C; 6.38%H; 7.71%N. Found: 75.59%H; 6.45%H; 7.64%N.

EXAMPLE 9

4.00 g of 2-Amino-N-ethyl-α-phenylphenethylamine dihydrochloride is heated in 14.4 ml of triethyl orthoacetate and 4.44 ml of acetic acid for 24 hours after which the solvents are removed first by distillation at atmospheric pressure, followed by distillation in vacuo (aspirator). The resulting oil is dissolved in 20 ml of 5% hydrochloric acid. The acidic mixture is poured onto 200 ml of water containing 20 ml of 37% hydrochloric acid. The biphasic mixture is washed with 100 ml of ether, basified with 50% sodium hydroxide solution and extracted with methylene chloride (2×200 ml). The combined extracts are dried over anhydrous magnesium sulate and evaporated affording a yellow oil. The oil is dissolved in 100 ml of ether. 10 ml of Ethereal hydrochloric acid is added precipitating the hydrochloride salt. The salt is collected and washed with hot acetone affording pale yellow crystals, mp 249°–252° C., of 4,5-dihydro-3-ethyl-2-methyl-4-phenyl-3H-1,3-benzodiazepine hydrochloride.

Analysis: Calculated for $C_{18}H_{20}N_2 \cdot HCl$: 71.87%C; 7.04%H; 9.31%N. Found: 71.57%C; 7.05%H; 9.20%N.

EXAMPLE 10

A mixture of 4 g of 2-Amino-N-methyl-α-(4-fluorophenyl)-phenethylamine, 5.6 ml of acetic acid and 18.33 ml of triethyl orthoacetate is refluxed for 2 hours. The solvents are evaporated in vacuo. The residue is combined with 5% hydrochloric acid and extracted with ether. The aqueous layer is basified and extracted with ether. The dried (anhydrous sodium sulfate) organic phase is filtered, ethereal hydrochloric acid is added dropwise to the filtrate and the product oils out. The solvent is evaporated and the residue recrystallized from ethanol-ether giving crystals, mp 253°–255° C., of 4,5-dihydro-2,3-dimethyl-4-(4-fluorophenyl)-3H-1,3-benzodiazepine hydrochloride.

Analysis: Calculated for $C_{17}H_{17}FN_2 \cdot HCl$: 66.99%C; 5.95%H; 9.19%N. Found: 66.69%C; 5.87%H; 9.01%N.

EXAMPLE 11

A mixture of 3 g of 2-amino-N-methyl-α-(4-methylphenyl)-phenethylamine dihydrochloride, 9.32 g of triethyl orthoacetate and 3.42 g of acetic acid is refluxed for 3 ½ hours. The solvent is evaporated and approximately 10 ml of 5% hydrochloric acid and 100 ml of water are added. The aqueous layer is extracted with ether. The aqueous layer is basified with 10% sodium hydroxide solution and extracted with ether. Ethereal hydrochloric acid is added and the product precipitates as the salt. Recrystallization from ethanol gives crystals, mp 285°–288° C., of 4,5-dihydro-2,3-dimethyl-α-(4-methylphenyl)-3H-1,3-benzodiazepine hydrochloride.

Analysis: Calculated for $C_{18}H_{20}N_2 \cdot HCl$: 71.87%C; 7.04%H; 9.31%N. Found: 71.85%C; 7.11%H; 9.28%N.

EXAMPLE 12

A stirred solution of 4.10 g of 2-amino-α-(4-methoxyphenyl)-N-methylphenethylamine, 16.22 g of triethyl orthoacetate and 5.6 ml of glacial acetic acid is held under reflux (bath temperature 112° C.) for 2 hours. AFter standing overnight at ambient temperature the solution is concentrated in vacuo (pump) at 90° C. on a rotary evaporator. An ethereal solution of the residual oil is washed with 5% hydrochloric acid. The aqueous phase is made alkaline with 50% sodium hydroxide solution and the mixture is extracted twice with 25 ml-portions of methylene chloride. The combined, (dried over anhydrous sodium sulfate) organic phase is evaporated to afford a solid. Recrystallization from 10 ml of acetonitrile provides tan crystals, mp 130°–132° C. of 4,5-dihydro-2,3-dimethyl-4-(4-methoxyphenyl)-3H-1,3-benzodiazepine.

Analysis: Calculated for $C_{18}H_{20}N_2O$: 77.12%C; 7.19%H; 9.99%N. Found: 77.20%C; 7.13%H; 10.05%N.

EXAMPLE 13

A stirred solution of 4.1 g of 2-amino-α-(4-methoxyphenyl)-N-methylphenethylamine, 17.6 g of triethyl orthopropionate and 5.6 ml of glacial acetic acid is heated under reflux for 3 hours with exclusion of moisture. After standing overnight at ambient temperature the solution is concentrated in vacuo (pump) at 90° C. on a rotary evaporator. A solution of the residual oil and 100 ml of methylene chloride is washed with 10% sodium hydroxide solution. The dried (over anhydrous sodium sulfate) organic phase is filtered and concentrated to an oil which is dissolved in 50 ml of anhydrous ether. Treatment with excess ethereal hydrogen chloride provides a precipitate which is collected, washed with ether and dried in vacuo at 40° C. Recrystallization from 40 ml of isopropanol provides colorless crystals, mp 240°–242° C. dec, of 4,5-dihydro-2-ethyl-4-(4-methoxyphenyl)-3-methyl-3H-1,3-benzodiazepine hydrochloride.

Anaylsis: Calculated for $C_{19}H_{22}N_2O \cdot HCl$: 68.98%C; 7.01%H; 8.47%N. Found: 68.66%C; 6.98%H; 8.30%N.

EXAMPLE 14

A stirred solution of 3.33 g of 2-amino-α-phenphenethylamine, 17.63 g of triethyl orthopropionate and 5.6 ml of glacial acetic acid is heated under reflux with exclusion of moisture for 2 ½ hours. Volatile components are removed on a rotary evaporator at 90° C. under reduced pressure (pump). A solution of the residual oil and 100 ml of methylene chloride is washed with 10% sodium hydroxide solution, dried over anhydrous sodium sulfate, filtered and concentrated to an oil. A solution of the oil and 70 ml of anhydrous ether is treated with excess ethereal hydrogen chloride. The precipitate is collected, washed with anhydrous ether and dried. Recrystallization from 90 ml of isopropanol provides colorless crystals, mp 242°–245° C., of 4,5-dihydro-2-ethyl-4-phenyl-3H-1,3-benzodiazepine hydrochloride.

Analysis: Calculated for $C_{17}H_{18}N_2 \cdot HCl$: 71.20%C; 6.68%H; 9.77%N. Found: 71.23%C; 6.65%H; 9.70%N.

EXAMPLE 15

A mixture of 3.5 g of α-(3,4-dimethoxyphenyl)-N-methyl-2-nitrophenethylamine, 11.9 g of triethyl orthoacetate and 4.6 ml of acetic acid is refluxed for 2 ½ hours. The solvents are evaporated and the residue partitioned between 5% hydrochloric acid and ether. The aqueous layer is separated, basified, extracted with ether and dried over anhydrous sodium sulfate. Ethereal hydrochloric acid is added to the filtered ether extract and the product oils out. The mixture is evaporated to dryness and the residue recrystallized from ethanol-ether, giving colorless crystals, mp 222°–226° C., of 4,5-dihydro-4-(3,4-dimethoxyphenyl)-2,3-dimethyl-3H-1,3-benzodiazepine hydrochloride.

Analysis: Calculated for $C_{19}H_{22}N_2O_2 \cdot HCl$: 65.89%C; 6.68%H; 8.08%N. Found: 65.84%C; 6.62%H; 8.06%N.

EXAMPLE 15A

A mixture of 1.1 g of N-acetyl-α-(3,4-dimethoxyphenyl)-N-methyl-2-aminophenethylamine in 40 ml of methylene chloride and 0.26 g of phosphorous oxychloride is refluxed 18 hours. The residue is basified with 10% sodium hydroxide solution and extracted with additional methylene chloride. The extract is dried (over anhydrous sodium sulfate) and evaporated. The residue is dissolved in absolute ethanol and ethereal hydrogen chloride is added. The product crystallizes on addition of the ethereal hydrogen chloride, ether giving colorless crystals, mp 220°–226° C., of 4,5-dihydro-4-(3,4-dimethoxyphenyl)-2,3-dimethyl-3H-1,3-benzodiazepine.

Analysis: Calculated for $C_{19}H_{22}N_2O_3 \cdot HCl$: 65.80%C; 6.68%H; 8.08%N. Found: 65.53%C; 6.70%H; 7.87%N.

EXAMPLE 16

A mixture of 4 g of 2-amino-N-methyl-α-(3,4-dimethoxyphenyl)-phenethylamine, 14.8 g of triethyl orthopropionate and 5.54 g of acetic acid is refluxed for 2 hours. The solvents are evaporated. The residue is dissolved in methylene chloride, washed with 5% sodium hydroxide solution and water and dried over anhydrous sodium sulfate, filtered and evaporated. The residue is dissolved in ether and ethereal hydrogen chloride is added dropwise. The product which precipitates as the hydrochloride salt is recrystallized from ethanol-ether giving tan crystals, mp 214°–216° C., of 4,5-dihydro-4-(3,4-dimethoxyphenyl)-2-ethyl-3-methyl-3H-1,3-benzodiazepine.

Analysis: Calculated for $C_{20}H_{24}N_2O_2 \cdot HCl$: 66.57%C; 6.98%H; 7.76%N. Found: 66.63%C; 6.93%H; 7.81%N.

EXAMPLE 17

3.00 g of N-Ethyl-2-nitro-α-phenylphenethylamine hydrochloride is treated with 100 ml of hot 95% ethanol containing 1.10 g of potassium hydroxide for 15 minutes, after which the mixture is filtered and placed in a Paar flask. 0.15 g of 10% palladium on charcoal is added and the mixture is hydrogenated at room temperature and 50 psia for 3 hours, after which the catalyst is removed. The ethanol is evaporated from the filtrate and the resulting yellow oil is poured onto 100 ml of water. The biphasic aqueous mixture is extracted with methylene chloride (2×100 ml). The combined methylene chloride extracts are dried over anhydrous magnesium sulfate and the methylene chloride evaporated to afford a colorless oil. The oil is dissolved in 50 ml of ether. Ethereal hydrogen chloride (100 ml) is added precipitating the hydrochloride acid salt as an oil. The ethanol is evaporated and the oil is dissolved in 20 ml of i-propanol with heating. Upon cooling, white crystals, mp >248° C. dec, fell from solution providing 2-amino-N-ethyl-α-phenylphenethylamine dihydrochloride.

Analysis: Calculated for $C_{16}H_{20}N_2 \cdot 2HCl$: 61.35%C; 7.08%H; 8.94%N. Found: 61.25%C; 7.11%H; 8.95%N.

EXAMPLE 18

3.34 g of 2-Nitro-α-phenyl-N-propylphenethylamine hydrochloride is heated in 100 ml of 95% ethanol containing 1.21 g of potassium hydroxide for 15 minutes, after which the precipitated sodium chloride is removed by filtration. The ethanolic filtrate is placed in a Paar flask containing 0.15 g of 10% palladium on charcoal and hydrogenated at 50 psia for 2 hours. The catalyst is then removed and the ethanol evaporated. The resulting yellow oil is poured onto 100 ml of water and the biphasic aqueous mixture is extracted with methylene chloride (2×100ml). The combined methylene chloride extracts are dried over anhydrous magnesium sulfate and the methylene chloride evaporated affording a yellow oil. The oil is dissolved in 50 ml of ethanol. Ethereal hydrogen chloride (50 ml) is added, precipitating the hydrochloride salt. The ethanol is evaporated and the resulting white powder is recrystallized from 20 ml of i-propanol to give crystals, mp > 243° C. dec, of 2-amino-α-phenyl-N-propylphenethylamine dihydrochloride.

Analysis: Calculated for $C_{17}H_{24}N_2Cl_2$: 62.39%C; 7.39%H; 8.56%N. Found: 62.16%C; 7.32%H; 8.49%N.

EXAMPLE 19

7.0 g of N-Cyclohexylmethyl-2-nitro-α-phenylphenethylamine hydrochloride is treated with 200 ml of warm 95% ethanol containing 2.07 of potassium hydroxide for 15 minutes, after which the mixture is filtered and placed in a Paar flask containing 0.35 g of 10% palladium on charcoal. The mixture is hydrogenated at 50 psia for 2 hours. After removal of the catalyst, the ethanol is evaporated and the resulting biphasic mixture is poured onto 200 ml of water. The aqueous mixture is extracted with methylene chloride (2×200 ml). The combined methylene chloride extracts are dried over anhydrous magnesium sulfate and the methylene chloride is evaporated giving a colorless oil. The oil is dissolved in 100 ml of ether. Ethereal hydrogen chloride (200 ml) is added and the salt precipitates from solution. The hydrochloride salt is collected as a gummy powder, which is recrystallized from i-propanol to provide crystals, mp 205° C. dec, of 2-amino-N-cyclohexylmethyl-α-phenylphenethylamine dihydrochloride.

Analysis: Calculated for $C_{21}H_{28}N_2 \cdot 2HCl$: 66.14%C; 7.93%H; 7.35%N. Found: 65.90%C; 7.86%H; 7.34%N.

EXAMPLE 20

To a mixture of 10 g of α-(4-methylphenyl)-N-methyl-2-nitro-phenethylamine and 150 ml of ethanol, 3.7 g of potassium hydroxide is added. The mixture is stirred for 15 minutes and the potassium chloride filtered off. The solution is hydrogenated at room temperature in the presence of 0.5 g of 10% palladium on charcoal for 2 hours. The catalyst is filtered off and ethereal-hydrogen chloride is added to the ethanolic filtrate. The mixture is evaporated and the residue is recrystallized from ethanol-ether giving crystals, mp 225°–228° C., of 2-amino-N-methyl-α-(4-methylphenyl)phenethylamine dihydrochloride.

Analysis: Calculated for $C_{16}H_{20}N_2 \cdot 2HCl$: 61.35%C; 7.08%H; 8.91%N. Found: 61.18%C; 7.02%H; 8.87%N.

EXAMPLE 21

A mixture of 10.02 g of α-(4-methoxyphenyl)-N-methyl-2-nitrophenethylamine hydrochloride, 100 ml of dichloromethane and 100 ml of water is treated with excess 10% sodium hydroxide solution. The dried (over anhydrous sodium sulfate) organic phase is concentrated to afford 8.74 g of a yellow oil. A mixture of the oil, 100 ml of absolute ethanol and 0.5 g of 10% palladium on charcoal catalyst is hydrogenated at 50 psia and ambient temperature on a Parr apparatus. Filtration and concentration of the filtrate on a rotary evaporator affords 10.35 g of an oil. A solution of the oil and 20 ml of methanol is treated with excess ethereal hydrogen chloride. Further dilution with ether affords a gum which solidifies on trituration with fresh ether. Recrystallization from 25 ml of isopropanol gives crystals, mp 223°–226° C. dec, of 2-amino-α-(4-methoxyphenyl)-N-methylphenethylamine dihydrochloride.

Analysis: Calculated for $C_{16}H_{20}N_2O \cdot 2HCl$: 58.37%C; 6.74%H; 8.51%N. Found: 58.11%C; 6.93%H; 8.36%N.

EXAMPLE 22

A 1 M solution of borane-tetrahydrofuran complex in tetrahydrofuran (42 ml) is added dropwise to a stirred cooled suspension of 6.00 g of N-acetyl-2-nitro-α-phenylphenethylamine in 60 ml of tetrahydrofuran. After complete addition the mixture is allowed to stir at room temperature for 24 hours, after which the excess borane is decomposed by the subsequent additions of 20 ml of 5% hydrochloric acid and 2 ml of acetic acid. The mixture is then basified with 20 ml of 50% sodium hydroxide solution. The tetrahydrofuran is evaporated from the biphasic mixture and the remaining aqueous phase is poured onto 100 ml of water. The aqueous mixture is extracted with methylene chloride (2×100 ml). The combined methylene chloride extracts are dried over anhydrous magnesium sulfate and evaporated to afford a yellow oil which is dissolved in 50 ml of ether. Ethereal hydrogen chloride (100 ml) is added precipitating the salt as an oil. The ether is evaporated and the remaining oil is dissolved in 20 ml of 100% ethanol and allowed to crystallize to provide crystals, mp 216°–225° C. dec, of N-ethyl-2-nitro-α-phenylphenethylamine hydrochloride.

Analysis: Calculated for $C_{16}H_{18}N_2O_2 \cdot HCl$: 62.64%C; 6.24%H; 9.13%N. Found: 62.53%C; 6.20%H; 9.22%N.

EXAMPLE 23

1 M borane-tetrahydrofuran complex (42 ml) is added dropwise to a cooled, stirred suspension of 6.00 g of 2-nitro-α-phenyl-N-propionylphenethylamine in 60 ml of tetrahydrofuran. After complete addition, the mixture is allowed to stir at room temperature for 24 hours after which the excess borane is decomposed by the successive additions of 20 ml of 5% hydrochloric acid and 2 ml of acetic acid. The acidic mixture is allowed to stir an additional 30 minutes, after which the mixture is basified with 20 ml of 50% sodium hydroxide solution. The mixture is then poured onto 100 ml of water and the aqueous phase extracted with methylene chloride 2×100 ml). The combined methylene chloride extracts are dried over anhydrous magnesium sulfate and the methylene chloride evaporated affording a yellow oil, which is dissolved in 50 ml of ether. Ethereal hydrogen chloride (100 ml ) is added precipitating the hydrochloride salt as an oil. The ether is evaporated and the resulting gum is dissolved in 40 ml of hot isopropanol. Upon cooling white crystals, mp 189°–192° C., of 2-nitro-α-phenyl-N-propylphenethylamine hydrochloride falls from solution.

Analysis: Calculated for $C_{17}H_{20}N_2O_2 \cdot HCl$: 63.65%C; 6.60%H; 8.73%N. Found: 63.64%C; 6.88%H; 8.38%N.

EXAMPLE 24

1 M Borane-tetrahydrofuran complex (60 ml) is added dropwise to a cooled, stirred solution of 9.00 g of N-benzoyl-2-nitro-α-phenylphenethylamine in 90 ml of tetrahydrofuran. After complete addition the mixture is stirred at room temperature for 4 hours. Additional tetrahydrofuran (100 ml) and 1 M borane-tetrahydrofuran complex (30 ml) are added to aid in the dissolution of the reactants. The mixture is allowed to stir at room temperature for 24 hours after which the excess borane is decomposed by the subsequent addition of 45 ml of 5% hydrochloric acid and 5 ml of acetic acid. The acidic mixture is stirred at room temperature for an additional 0.5 hours after which 25 ml of 50% sodium hydroxide solution is added. The tetrahydrofuran is evaporated from the mixture and the resulting aqueous mixture is poured onto 125 ml of water. The aqueous phase is extracted with methylene chloride (1×150 ml; 1×100 ml). The combined methylene chloride extracts are dried over anhydrous magnesium sulfate and evaporated to give a solid which recrystallizes from 150 ml of 100% ethanol giving flocullant crystals. The ethanolic filtrate is acidified with 100 ml of ethereal hydrogen chloride. Upon prolonged standing the hydrochloric salt falls from solution. Recrystallization of the salt from 40 ml of ethanol gives yellow granules, mp 215°–218° C., of N-benzyl-2-nitro-α-phenylphenethylamine hydrochloride.

Analysis: Calculated for $C_{21}H_{20}N_2O_2 \cdot HCl$: 68.38%C; 5.74%H; 7.59%N. Found: 68.11%C; 5.58%H; 7.66%N.

EXAMPLE 25

1 M Borane-tetrahydrofuran complex (60 ml) is added dropwise to a stirred, cooled suspension of 9.00 g of N-cyclohexylcarbonyl-2-nitro-α-phenylphenethylamine in 90 ml of tetrahydrofuran. After complete addition the mixture is allowed to stir for 4 hours. Additional borane (30 ml) and tetrahydrofuran (100 ml) is added to complete dissolution of materials. The mixture is stirred an additional 16 hours. After cooling of the mixture, the excess borane is decomposed by the subsequent additions of 45 ml of 5% hydrochloric acid and 4 ml of acetic acid. The mixture is stirred for ½ hour before the addition of 25 ml of 50% sodium hydroxide solution. The tetrahydrofuran is evaporated from the mixture and the resulting biphasic mixture is poured onto 125 ml of water. The aqueous mixture is extracted with methylene chloride (1×150 ml, 1×100 ml). The combined methylene chloride extracts are dried over anhydrous magnesium sulfate and the methylene chloride is evaporated giving a yellow oil. The oil is dissolved in 100 ml of ether. Ethereal hydrogen chloride (200 ml) is added. Upon standing, a white precipitate falls from solution. The ether is evaporated and the solid is recrystallized from 50 ml of ethanol giving crystals, mp 225°-228° C., of N-cyclohexylmethyl-2-nitro-α-phenylphenethylamine hydrochloride.

Analysis: Calculated for $C_{21}H_{26}N_2O_2 \cdot HCl$: 67.28%C; 7.26%H; 7.47%N. Found: 67.08%C; 7.26%H; 7.51%N.

EXAMPLE 26

A stirred ice water chilled suspension of 12.3 g of N-formyl-α-(4-methoxyphenyl)-2-nitrophenethylamine and 120 ml of tetrahydrofuran is treated over 20 minutes with 85 ml of 1.01 M borane in tetrahydrofuran. After total addition the solution is stirred for 3 hours with ice water cooling and then allowed to stand 2 days at ambient temperature with exclusion of moisture. The stirred solution is chilled and quenched by dropwise addition of 40 ml of 5% hydrochloric acid and 4 ml of glacial acetic acid. Two hours after total addition the mixture is made alkaline with 50% sodium hydroxide solution, diluted with 50 ml of water and concentrated on a rotary evaporator to removed the tetrahydrofuran. The residual liquid is extracted thrice with 70 ml portions of dichloromethane and the combined organic phase is dried over anhydrous sodium sulfate, filtered and concentrated to an oil. A solution of the oil and 100 ml of ether is treated with ethereal hydrogen chloride giving a gum. The ether-gum mixture is evaporated to a yellow colored amorphorous foam which is recrystallized from isopropanol to provide almost colorless crystals, mp 181°-185° C., of α-(4-methoxyphenyl)-N-methyl-2-nitrophenethylamine hydrochloride.

Analysis: Calculated for $C_{16}H_{18}N_2O_3 \cdot HCl$: 59.54%C; 5.93%H; 8.68%N. Found: 59.24%C; 5.81%H; 8.65%N.

EXAMPLE 27

To a cooled mixture of 33.6 g of N-formyl-α-(4-methoxyphenyl)-2-nitrophenethylamine in 500 ml of tetrahydrofuran, 408 ml of 0.98 M of boron hydride/tetrahydrofuran is added dropwise keeping the internal temperature at 0°-10° C. The mixture is allowed to stand overnight at ambient temperature. To the cooled mixture 100 ml of 5% hydrochloric acid is added cautiously, followed by addition of 20 ml of glacial acetic acid. The solvent is evaporated in vacuo and the residue treated with 10% sodium hydroxide solution. The free base is extracted with ether, dried over anhydrous sodium sulfate and filtered. The product is precipitated as the hydrochloride salt by addition of ethereal hydrogen chloride to the ether extract. Recrystallization from ethanol gives crystals, mp 185°-187.5° C., of α-(3,4-dimethoxyphenyl)-N-methyl-2-nitrophenethylamine hydrochloride.

Analysis: Calculated for $C_{17}H_{20}N_2O_4 \cdot HCl$: 57.87%C; 6.00%H; 7.94%N. Found: 57.77%C; 6.09%H; 7.93%N.

EXAMPLE 28

To a cooled mixture of 31.1 g of N-formyl-α-(4-fluorophenyl)-2-nitrophenethylamine in 500 ml of tetrahydrofuran, 441 ml of 0.98 M borane in tetrahydrofuran is added dropwise. The mixture is allowed to stand over the weekend. The mixture is cooled and 100 ml of 5% hydrochloric acid and 20 ml of glacial acetic acid are added cautiously. The solvent is evaporated in vacuum and the residue treated with 10% sodium hydroxide solution. The free amine is extracted with ether and dried over anhydrous sodium sulfate and filtered. Ethereal hydrogen chloride is added dropwise to the filtrate and the product precipitates as the hydrochloride salt. Recrystallization from ethanol gives crystals, mp 241°-243° C., of α-(4-fluorophenyl)-N-methyl-2-nitrophenethylamine hydrochloride.

Analysis: Calculated for $C_{15}H_{15}FN_2O_2 \cdot HCl$: 57.98%C; 4.87%H; 9.01%N. Found: 57.89%C; 5.15%H; 9.01%N.

EXAMPLE 29

To a cooled solution of 17 g of N-formyl-α-(4-methyl-phenyl)-2-nitrophenethylamine in 200 ml of tetrahydrofuran, 122 ml of 0.98 M borane in tetrahydrofuran is added dropwise in an atmosphere of nitrogen. The temperature did not exceed 10° C. during the addition. The mixture is allowed to stir at room temperature for 4 hours. Excess borane is decomposed by addition of 50 ml of 5% hydrochloric acid and 10 ml of acetic acid. The mixture is allowed to stand over the weekend. Tetrahydrofuran is evaporated in vacuo. The residue is treated with 10% sodium hydroxide solution, extracted with ether and the organic phase is dried over anhydrous sodium sulfate and filtered. Ethereal hydrogen chloride is added to the filtrate and the hydrochloride salt precipitates. Recrystallization from ethanol yields crystals, mp 235°-238° C., of α-(4-methylphenyl)-N-methyl-2-nitrophenethylamine hydrochloride.

Analysis: Calculated for $C_{16}H_{18}N_2O_2 \cdot HCl$: 62.64%C; 6.24%H; 9.13%N. Found: 62.50%C; 6.23%H; 9.14%N.

EXAMPLE 30

A stirred ice water chilled solution of 27.8 g of 1-(4-methoxyphenyl)-2-(2-nitrophenyl)ethanone oxime acetate and 250 ml of tetrahydrofuran is treated over 30 minutes with 360 ml of 0.94 M borane in tetrahydrofuran (four-fold excess of boron hydride). After total addition, the solution is stirred for 1 hour at ice-bath temperature, followed by stirring at ambient temperature for 4 hours. The solution is then allowed to stand for 2 days at ambient temperature. The stirred solution is chilled with an ice water bath and quenched by dropwise addition of 100 ml of 5% hydrochloric acid. A colorless precipitate separates and the mixture is stirred for 2 hours with cooling. Glacial acetic acid (15 ml) is added, followed by stirring for 2 hours and then standing overnight at ambient temperature. The stirred suspension is then treated with 300 ml of 10% sodium hydroxide solution, followed by removal of excess tetrahydrofuran on a rotary evaporator. The residual biphasic mixture is extracted thrice with 200 ml-portions of methylene chloride. The combined organic phase is dried over anhydrous sodium sulfate, vacuum filtered and evaporated to an orange colored oil. A solution of the oil and 200 ml of anhydrous ether is treated with a slight excess of ethereal hydrogen chloride. The precipitate is collected by vacuum filtration. The filter cake is washed twice with ether and dried in vacuo at 40° C. over sodium hydroxide pellets. Recrystallization of the crude product from 600 ml of 95% ethanol gives 16.1 g of slightly yellow crystals, mp 240°-242° C., of α-(4-methoxyphenyl)-2-nitrophenethylamine hydrochloride.

Analysis: Calculated for $C_{15}H_{16}N_2O_3 \cdot HCl$: 58.35%C; 5.55%H. Found: 58.21%C; 5.25%H.

EXAMPLE 31

To a cooled solution of 48 g of 1-(4-methylphenyl)-2-(2-nitrophenyl)-ethanone oxime acetate in 350 ml of tetrahydrofuran in an atmosphere of nitrogen, 594 ml 1.01 M borane in tetrahydrofuran is added dropwise. The internal temperature remains approximately 0°–20° C. during the addition. The mixture is stirred for 45 minutes at ice bath temperature and then stirred overnight at ambient temperature. The mixture is cooled and the complex is decomposed by cautious addition of 6N hydrochloric acid. A precipitate gradually forms and the mixture is stirred overnight. Tetrahydrofuran is evaporated in vacuum and 10% sodium hydroxide solution is added to the residue. The product is extracted with ether and dried over anhydrous sodium sulfate. Ethereal hydrogen chloride is added to the solution and the product precipitates as the hydrochloride salt. Recrystallization from ethanol gives crystals, mp 265°–269° C., of α-(4-methylphenyl)-2-nitrophenethylamine hydrochloride.

Analysis: Calculated for $C_{15}H_{16}N_2O_2 \cdot HCl$: 61.54%C; 5.85%H; 9.57%N. Found: 61.57%C; 6.00%H; 9.44%N.

EXAMPLE 32

To a cooled mixture of 92.6 g of 1-(3,4-dimethoxyphenyl)-2-(2-nitrophenyl)ethanone oxime acetate in 600 ml of tetrahydrofuran in an atmosphere of nitrogen, a solution of 1019 ml of 0.98 M borane in tetrahydrofuran is added dropwise. The mixture is allowed to stand overnight at ambient temperature. The mixture is cooled and 250 ml of 5% hydrochloric acid is added dropwise. The solvent is evaporated in vacuo and the residue treated with 10% sodium hydroxide solution. The free amine is extracted with ether, dried over anhydrous sodium sulfate and filtered. Ethereal hydrogen chloride is added dropwise to the filtrate and the product precipitates as the hydrochloride salt. Recrystallization from methanolether gives crystals, mp 229°–231° C., of α-(3,4-dimethoxyphenyl)-2-nitrophenethylamine hydrochloride.

Analysis: Calculated for $C_{16}H_{18}N_2O_4 \cdot HCl$: 56.73%C; 5.65%H; 8.27%N. Found: 56.63%C; 5.65%H; 8.22%N.

EXAMPLE 33

In an atmosphere of nitrogen, 897 ml of 0.98 M borane in tetrahydrofuran is added dropwise to a cooled solution of 69.2 g of 1-(4-fluorophenyl)-2-(2-nitrophenyl)ethanone oxime acetate in 500 ml of tetrahydrofuran. The mixture is allowed to stand over the weekend. The mixture is cooled and 200 ml of 5% hydrochloric acid is added dropwise. The tetrahydrofuran is evaporated and the residue treated with 10% sodium hydroxide solution. The free amine is extracted with ether and dried over anhydrous sodium sulfate. The ether solution is treated with ethereal hydrogen chloride and the product is recrystallized from ethanol to give crystals, mp 239°–243° C., of α-(4-fluorophenyl)-2-nitrophenethylamine hydrochloride.

Analysis: Calculated for $C_{14}H_{13}FN_2O_2 \cdot HCl$: 56.67%C; 4.76%H; 9.44%N. Found: 56.86%C; 4.70%H; 9.36%N.

EXAMPLE 34

10.0 g of 2-nitro-α-phenylphenethylamine in 75 ml of toluene is added in a dropwise manner to a cooled, stirred solution of 10.2 ml of acetic anhydride in 100 ml of toluene. Upon completion of addition, the mixture is allowed to remain at room temperature for 72 hours, after which the precipitate is collected, washed with ether (2×50 ml) and dried. Recrystallization from 100% ethanol gives crystals, mp 171°–172° C., of N-acetyl-2-nitro-α-phenylphenethylamine.

Analysis: Calculated for $C_{16}H_{16}N_2O_3$: 67.59%C; 5.67%H; 9.85%N. Found: 67.50%C; 5.61%H; 9.95%N.

EXAMPLE 35

10.0 g of 2-nitro-α-phenylphenethylamine in 75 ml of toluene is added in a dropwise manner to a cooled, stirred solution of 10.5 ml of propionic anhydride in 100 ml of toluene. Upon completion of addition, the mixture is allowed to remain at room temperature for 75 hours, after which the precipitate is collected, washed with ether (2×50 ml) and dried to give white powder. Recrystallization from 100% ethanol-water (0 ml–30 ml) gives pale yellow needles, mp 149°–151° C., of N-propionyl-2-nitro-α-phenylphenethylamine.

Analysis: Calculated for $C_{17}H_{18}N_2O_3$: 68.44%C; 6.08%H; 9.39%N. Found: 68.30%C; 5.94%H; 9.26%N.

EXAMPLE 36

10.0 g of 2-nitro-α-phenylphenethylamine in 75 ml of toluene is added dropwise to a stirred, cooled solution of 24.3 g of benzoic anhydride in 75 ml of toluene. After complete addition, the mixture is stirred at room temperature for 2 hours after which the precipitate is collected, washed with 300 ml of ether and partially dried. The precipitate is heated in boiling (400 ml)ethanol, cooled and collected giving white needles, mp 185°–189° C., of N-benzoyl-2-nitro-α-phenylphenethylamine.

Analysis: Calculated for $C_{21}H_{18}N_2O_2$: 72.82%C; 5.24%H; 8.09%N. Found: 72.54%C; 5.29%H; 8.07%N.

EXAMPLE 37

10.0 g of 2-nitro-α-phenylphenethylamine in 75 ml of toluene is added dropwise to a stirred, cooled solution of 14.4 ml of cyclohexylcarbonyl chloride in 75 ml of toluene and 25 ml of pyridine. After complete addition the mixture is stirred at room temperature for 2 hours. The mixture is allowed to stand overnight, after which the tan precipitate is collected and washed with 100 ml of ether. The precipitate is recrystallized from 350 ml of methanol to give yellow needles, mp 210°–212° C., of N-cyclohexanecarbonyl-2-nitro-α-phenylphenethylamine.

Analysis: Calculated for $C_{21}H_{24}N_2O_3$: 71.57%C; 6.86%H; 7.95%N. Found: 71.36%C; 6.92%H; 7.99%N.

EXAMPLE 38

A suspension of 14.0 g of α-(4-methoxyphenyl)-2-nitrophenethylamine hydrochloride, and 250 ml of water is treated with 70 ml of 10% sodium hydroxide solution. The mixture is twice extracted with 200 ml-portions of methylene chloride and the combined organic phase is dried over anhydrous sodium sulfate. Vacuum filtration and concentration affords 12.7 g of a yellow-colored oil. A solution of the oil and 200 ml of methyl formate is heated at 80°–83° C. (bath temperature) for 3 days in a 300 ml Parr stainless steel bomb. After cooling to room temperature the bomb is opened and the crystalline precipitate is collected by vacuum filtration. The filter cake is washed once with methylformate and dried in vacuo at 40° C. to give slightly yellow-colored crystals, mp 151°–153° C., of N-formyl-α-(4-methoxyphenyl)-2-nitrophenethylamine.

Analysis: Calculated for $C_{16}H_{16}N_2O_4$: 63.99%C; 5.37%H; 9.33%N. Found: 63.92%C; 5.29%H; 9.37%N.

EXAMPLE 39

A mixture of 19.6 g of α-(4-methylphenyl)-2-nitrophenethylamine and 230 ml of methyl formate is placed in a Parr bomb at 80° C. overnight. The reaction is cooled and the solvent removed in vacuo giving an off-white solid. The product is recrystallized from 95% ethanol giving crystals, mp 130°–132° C., of N-formyl-α-(4-methylphenyl)-2-nitrophenethylamine.

Analysis: Calculated for $C_{16}H_{16}N_2O_3$: 67.59%C; 5.67%H; 9.85%N. Found: 67.58%C; 5.63%H; 9.94%N.

EXAMPLE 40

A mixture of 36.6 g of α-(4-fluorophenyl)-2-nitrophenethylamine and 230 ml of methylformate in a Parr bomb is placed in an oil bath at 80° C. and left over the weekend. On cooling a crystalline precipitate separates giving 34.6 g of product. An analytical sample is recrystallized from 95% ethanol providing crystals, mp 142°–145° C., of N-formyl-α-(4-fluorophenyl)-2-nitrophenethylamine.

Analysis: Calculated for $C_{15}H_{13}FN_2O_3$: 62.50C; 4.54% H; 9.72% N. Found: 62.62% C; 4.51% H; 9.77% N.

EXAMPLE 41

A mixture of 41.7 g of α-(3,4-dimethoxyphenyl)-2-nitrophenethylamine and 250 ml of methylformate is placed in a Parr bomb at 80° C. and left overnight. The solvent is evaporated and the residue recrystallized from 95% ethanol giving crystals, mp 135°–139° C., of N-formyl-α-(3,4-dimethoxyphenyl)-2-nitrophenethylamine.

Analysis: Calculated for $C_{17}H_{18}N_2O_5$: 61.81% C; 5.49% H; 8.48% N. Found: 61.67% C; 5.27% H; 8.42% N.

EXAMPLE 42

To a cooled solution of 4.17 g of acetic anhydride in 50 ml of toluene, a solution of 4.31 g of α-(3,4-dimethoxyphenyl)-N-methyl-2-nitrophenethylamine is added dropwise. The mixture is warmed to room temperature and stirred for 2 hours. The solvents are evaporated in vacuo to give crystals, mp 113°–115° C., of N-acetyl-α-(3,4-dimethoxyphenyl)-N-methyl-2-nitrophenethylamine.

Analysis: Calculated for $C_{19}H_{22}N_2O_5$: 63.67% C; 6.18% H; 7.82% N. Found: 63.68% C; 6.20% H; 7.76% N.

EXAMPLE 43

A mixture of 12.3 g of 2'-fluoro-2-(2-nitrophenyl)acetophenone in 80 ml of 95% ethanol, 6.6 g of hydroxylamine hydrochloride in 20 ml of water and 8.53 g of sodium acetate in 20 ml of water is refluxed overnight. The product crystallizes on cooling. Recrystallization from 95% ethanol gives crystals, mp 105°–109° C., of 1-(2-fluorophenyl)-2-(2-nitrophenyl)ethanone oxime.

Analysis: Calculated for $C_{14}H_{11}FN_2O_3$: 61.31% C; 4.04% H; 10.21% N. Found: 61.19% C; 4.09% H; 10.25% N.

EXAMPLE 44

A mixture of 154 g of 1-(3,4-dimethoxyphenyl)-2-(2-nitrophenyl)ethanone in 600 ml of 95% ethanol, 70.9 g of hydroxylamine hydrochloride in 150 ml of water and 92 g of sodium acetate in 150 ml of water is refluxed 7 hours. The product which crystallizes on standing overnight at room temperature is filtered and dried giving crystals, mp 129°–130° C., of 1-(3,4-dimethoxyphenyl)-2-(2-nitrophenyl)ethanone oxime.

Analysis: Calculated for $C_{16}H_{16}N_2O_5$: 60.75% C; 5.10% H; 8.85% N. Found: 60.75% C; 5.15% H; 8.84% N.

EXAMPLE 45

A stirred suspension of 46.0 g of 1-(4-methoxyphenyl)-2-(2-nitrophenyl)ethanone and 240 ml of 95% ethanol is treated with a solution of 22.6 g of hydroxylamine hydrochloride, 46.3 g of sodium acetate trihydrate and 130 ml of water. The stirred suspension is heated to reflux and 95% ethanol (180 ml) is added. The mixture is heated for 3 hours under reflux whereupon a clear yellow-colored solution is obtained. After stirring overnight at ambient temperature, excess ethanol is removed on a rotary evaporator and the residue is diluted with approximately 1 l. of water. An oil separates and crystallizes. The solid is collected, washed with water and dried at 40° C. overnight in vacuo. Recrystallization from 100 ml of 95% ethanol provides crystals, mp 106°–110° C., of 1-(4-methoxyphenyl)-2-(2-nitrophenyl)ethanone oxime.

Analysis: Calculated for $C_{15}H_{14}N_2O_4$: 62.93% C; 4.93% H. Found: 62.95% C; 4.93% H.

EXAMPLE 46

To a solution of 6.62 g of 1-(4-fluorophenyl)-2-(2-nitrophenyl)-ethanone in 40 ml of 95% ethanol, 3.55 g of hydroxylamine hydrochloride in 10 ml of water and 4.48 g of sodium acetate in 10 ml of water are added. The mixture is refluxed 3 hours and allowed to stand overnight. The ethanol is removed in vacuo and the product is extracted with ether, dried over anhydrous sodium sulfate and evaporated. Recrystallization from 95% ethanol gives crystals, mp 139°–142° C., of 1-(4-fluorophenyl)-2-(2-nitrophenyl)-ethanone oxime.

Analysis: Calculated for $C_{14}H_{11}FN_2O_3$: 61.31% C; 4.04% H; 10.21% N. Found: 61.15% C; 4.08% H; 10.27% N.

EXAMPLE 47

To a mixture of 50 g of 1-(4-methylphenyl)-2-(2-nitrophenyl)-ethanone in 200 ml of 95% ethanol, a solution of 27.8 g of hydroxylamine hydrochloride in 50 ml of water and a solution of 36.1 g of sodium acetate are added. The reaction mixture is refluxed for 3 hours and allowed to stand overnight at ambient temperature. The product which crystallizes from the reaction mixture is filtered and dried. Recrystallization from 95% ethanol provides crystals, mp 129°–132° C., of 1-(4-methylphenyl)-2-(2-nitrophenyl)ethanone oxime.

Analysis: Calculated for $C_{15}H_{14}N_2O_3$: 66.66% C; 5.22% H; 10.36% N. Found: 66.59% C; 5.31% H; 10.45% N.

EXAMPLE 48

A mixture of 156 g of 1-(3,4-dimethoxyphenyl)-2-(2-nitrophenyl)ethanone oxime and 100 g of acetic anhydride is warmed on a steam bath for 30 minutes. The product crystallizes on standing overnight at room temperature. Trituration with hexane gives crystals, mp 118°–120° C., of 1-(3,4-dimethoxyphenyl)-2-(2-nitrophenyl)ethanone oxime acetate.

Analysis: Calculated for $C_{18}H_{18}N_2O_6$: 60.37% C; 5.06% H; 7.82% N. Found: 60.14% C; 5.11% H; 7.78% N.

EXAMPLE 49

A stirred solution of 15.0 g of 1-(4-methoxyphenyl)-2-(2-nitrophenyl)ethanone oxime and 30 ml of potassium hydroxide dried pyridine is treated dropwise with 15.0 ml of acetic anhydride. After stirring overnight at ambient temperature with exclusion of moisture, the solution is heated for 2 hours on a steam bath. The solution is then decanted into 300 ml of ice water and the resultant biphasic mixture is extracted with a total of 270 ml of methylene chloride. The organic phase is washed once with dilute acetic acid (18 ml of glacial acetic acid diluted with 200 ml of water) and then twice with water. Concentration of the dried (over anhydrous sodium sulfate) organic phase affords 21.0 g of yellow oil. A solution of the oil and 125 ml of ether is washed sequentially with 50 ml-portions each of 5% hydrochloric acid solution, water, 5% sodium bicarbonate solution and water. The (dried over anhydrous sodium sulfate)organic phase is concentrated to a cloudy yellow oil which is subjected to azeotropic distillation with absolute ethanol. On standing overnight at ambient temperature, small rosettes of crystals form and a rosette is removed for use as seed crystals. The remaining material is dissolved in 40 ml of 95% ethanol, cooled slowly until an oil begins to separate and seeded with the previously isolated crystals. The crystalline precipitate is collected by vacuum filtration, washed with 95% ethanol and dried in vacuo to provide crystals, mp 65°–68.5° C., of 1-(4-methoxyphenyl)-2-(2-nitrophenyl)ethanone oxime acetate.

Analysis: Calculated for $C_{17}H_{16}N_2O_5$: 62.19% C; 4.91% H. Found: 62.16% C; 4.85% H.

EXAMPLE 50

To a solution of 47.3 g of 1-(4-methylphenyl)-2-(2-nitrophenyl)ethanone oxime in 100 ml of pyridine, 40 ml of acetic anhydride is added dropwise. The mixture is warmed on the steam bath (internal temperature approximately 80° C.) for 1 hour. The mixture is poured into water and the product which crystallizes is filtered giving crystals, mp 95°–98° C., of 1-(4-methylphenyl)-2-(2-nitrophenyl)ethanone oxime acetate.

Analysis: Calculated for $C_{17}H_{16}N_2O_4$: 65.38% C; 5.20% H; 8.97% N. Found: 65.42% C; 5.16% H; 9.00% N.

EXAMPLE 51

To a solution of 72.7 g of 1-(4-fluorophenyl)-2-(2-nitrophenyl)ethanone oxime in 175 ml of pyridine, 70 ml of acetic anhydride is added dropwise. The mixture is warmed on the steam bath for 1½ hours. The reaction mixture is poured into ice water and the solution made slightly acid with hydrochloric acid. The material which precipitates is filtered, dried and recrystallized from 95% ethanol giving crystals, mp 74°–75° C., of 1-(4-fluorophenyl)-2-(2-nitrophenyl)ethanone oxime acetate.

Analysis: Calculated for $C_{16}H_{13}FN_2O_4$: 60.76% C; 4.14% H; 8.86% N. Found: 60.66% C; 4.13% H; 8.78% N.

EXAMPLE 52

To a solution of 8 g of 1-(2-fluorophenyl)-2-(2-nitrophenyl)-ethanone oxime in 20 ml of pyridine, 10 ml of acetic anhydride is added dropwise. The mixture is warmed (steam bath) for 3½ hours, poured into water and extracted with methylene chloride. The methylene chloride extract is washed with 5% hydrochloric acid, dried over anhydrous sodium sulfate, filtered and evaporated. The residual oil is distilled at 5 mm to give 1-(2-fluorophenyl)-2-(2-nitrophenyl)ethanone oxime acetate, bp 133°–135° C.

Analysis: Calculated for $C_{16}H_{13}FN_2O_4$: 60.76% C; 4.14% H; 8.86% N. Found: 60.83% C; 4.09% H; 9.11% N.

EXAMPLE 53

To a mixture of 10 g of o-nitrophenylacetic acid in 29 ml of fluorobenzene, 4.3 of thionyl chloride is added dropwise at room temperature. The mixture is warmed at 45° C. for 3½ hours. To the cooled solution 8.1 g of aluminum chloride is added in portions. During the addition there is a slight exothermic reaction and the temperature rose to 40° C. The mixture is warmed to 45° C. for approximately 1½ hours. The reaction mixture is poured into concentrated hydrochloric acid-ice and extracted with ether. The ether extract is washed with 5% sodium hydroxide solution, water, dried over anhydrous sodium sulfate and evaporated to give a crude solid. Recrystallization from 95% ethanol gives crystals, mp 80°–81° C., of 1-(4-fluorophenyl)-2-(2-nitrophenyl)ethanone.

Analysis: Calculated for $C_{14}H_{10}FNO_3$: 64.86% C; 3.89% H; 5.40% N. Found: 64.64% C; 3.94% H; 5.31% N.

EXAMPLE 54

To a mixture of 181 g of o-nitrophenylacetic acid in 400 ml of 1,2-dichloroethane, 78 ml of thionyl chloride is added dropwise at room temperature. The mixture is warmed to approximately 65° C. then allowed to stand overnight at ambient temperature. To 400 ml of m-fluorotoluene, 133 g of aluminum chloride is added in portions followed by the dropwise addition of the acid chloride solution keeping the temperature approximately 20°–25° C. The mixture is gradually warmed to 60° C. and held at 60° C. until gas evolution ceases. The reaction mixture is poured into concentrated hydrochloric acid and ice and allowed to stand over the weekend. Additional methylene chloride is added to the reaction mixture. The organic layer is separated, washed with 5% sodium hydroxide solution and water, dried over anhydrous sodium sulfate and filtered. Evaporation of the filtrate gives a black oil. The oil is extracted with boiling isopropyl ether which on cooling yields product. Recrystallization from hexane provides crystals, mp 72°–74° C., of 1-(4-fluoro-2-methylphenyl)-2-(2-nitrophenyl)ethanone.

Analysis: Calculated for $C_{15}H_{12}FNO$: 65.93% C; 4.43% H; 5.13% N. Found: 66.01% C; 4.47% H; 5.10% N.

EXAMPLE 55

A mixture of 46 g of α-(4-chlorobenzoyl)-β-dimethylamino-2-nitrostyrene, 150 ml of dioxane and 50 ml of water is heated under reflux for 18 hours. The solution is concentrated. The residue is extracted with methylene chloride, dried over anhydrous sodium sulfate and evaporated to an oil. The oil is dissolved in a small volume of 95% ethanol and the product crystallizes. Recrystallization from ethanol gives crystals, mp 70°–72° C., of 1-(4-chlorophenyl)-2-(2-nitrophenyl)ethanone.

Analysis: Calculated for $C_{14}H_{10}ClNO_3$: 61.00% C; 3.66% H; 5.08% N. Found: 60.96% C; 3.68% H; 5.15% N.

EXAMPLE 56

To a solution of 39.7 g of β-dimethyl-amino-2-nitrostyrene and 21.2 g of triethylamine in 150 ml of benzene is added dropwise 36.8 g of p-chlorobenzoyl chloride. The resultant mixture is stirred and heated under reflux for 15 hours. Water is added to dissolve the salts. The product crystallizes and is filtered off. On concentration of the filtrate, additional product crystallizes as bright orange crystals, 50 g (72%). An analytical sample is recrystallized from 95% ethanol, mp 142°–148° C. to give α-(4-chlorobenzoyl)-β-dimethylamino-2-nitrostyrene.

Analysis: Calculated for $C_{17}H_{15}ClN_2O_3$: 61.73% C; 4.57% H; 8.47% N. Found: 61.65% C; 4.58% H; 8.36% N.

EXAMPLE 57

A solution of 3.8 g of N-acetyl-α-(3,4-dimethoxyphenyl)-N-methyl-2-nitrophenethylamine in 100 ml of ethanol is hydrogenated at room temperature and 50 psia over 0.5 g of 10% palladium on charcoal for approximately 20 minutes. The catalyst is filtered and the solvent evaporated giving product. Recrystallization from 95% ethanol gave crystals, mp 139°–142° C., of N-acetyl-2-amino-α-(3,4-dimethoxyphenyl)-N-methylphenethylamine.

Analysis: Calculated for $C_{19}H_{24}N_2O_3$: 69.53% C; 7.37% H; 8.53% N. Found: 69.67% C; 7.33% H; 8.56% N.

We claim:

1. A compound of the formula

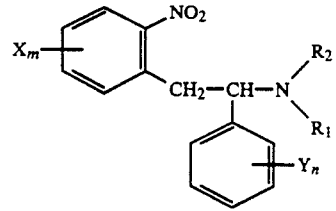

in which $R_1$ is hydrogen, alkyl of from 1 to 5 carbon atoms, cycloalkylalkyl of from 4 to 8 carbon atoms or aralkyl having 1 to 5 carbon atoms in the alkyl moiety; $R_2$ is a group of the formula

wherein $R_3$ is hydrogen, alkyl of from 1 to 4 carbon atoms, cycloalkyl of from 3 to 7 carbon atoms or aryl; X and Y are the same or different and each can be hydrogen, chlorine, bromine, fluorine, methoxy, alkyl of from 1 to 3 carbon atoms, hydroxy or trifluoromethyl; m is the integer 1 or 2 and n is the integer 1,2 or 3.

2. A compound as defined in claim 1 in which $R_1$ is alkyl of from 1 to 5 carbon atoms.

3. A compound as defined in claim 2 in which $R_1$ is methyl or ethyl.

4. The compound defined in claim 1 which is N-acetyl-2-nitro-α-phenylphenethylamine.

5. The compound defined in claim 1 which is N-propionyl-2-nitro-α-phenylphenethylamine.

6. The compound defined in claim 1 which is N-benzoyl-2-nitro-α-phenylphenethylamine.

7. The compound defined in claim 1 which is N-cyclohexanecarbonyl-2-nitro-α-phenylphenethylamine.

8. The compound defined in claim 1 which is N-formyl-α-(4-methoxyphenyl)-2-nitrophenethylamine.

9. The compound defined in claim 1 which is N-formyl-α-(4-methylphenyl)-2-nitrophenethylamine.

10. The compound defined in claim 1 which is N-formyl-α-(4-fluorophenyl)-2-nitrophenethylamine.

11. The compound defined in claim 1 which is N-formyl-α-(3,4-dimethoxyphenyl)-2-nitrophenethylamine.

12. The compound defined in claim 1 which is N-acetyl-α-(3,4-dimethoxyphenyl)-N-methyl-2-nitrophenethylamine.

13. The compound defined in claim 1 which is N-formyl-2-nitro-α-phenylphenethylamine.

* * * * *